US008265554B2

(12) United States Patent
Hwang et al.

(10) Patent No.: US 8,265,554 B2
(45) Date of Patent: Sep. 11, 2012

(54) COMMUNICATION DEVICE AND METHOD USING HUMAN BODY

(75) Inventors: Jung-Hwan Hwang, Daejeon (KR); Sung-Weon Kang, Daejeon (KR); Chang-Hee Hyoung, Daejeon (KR); Jin-Bong Sung, Daejeon (KR); Duck-Gun Park, Daejeon (KR); Jin-Kyung Kim, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 542 days.

(21) Appl. No.: 12/300,818

(22) PCT Filed: May 29, 2007

(86) PCT No.: PCT/KR2007/002600
§ 371 (c)(1),
(2), (4) Date: Nov. 14, 2008

(87) PCT Pub. No.: WO2007/148877
PCT Pub. Date: Dec. 27, 2007

(65) Prior Publication Data
US 2009/0233558 A1   Sep. 17, 2009

(30) Foreign Application Priority Data
Jun. 20, 2006 (KR) .................. 10-2006-0055448

(51) Int. Cl.
*H04B 5/00* (2006.01)
(52) U.S. Cl. ........... 455/41.1; 455/67.14; 340/5.64; 341/33; 702/150
(58) Field of Classification Search ............... 455/41.1, 455/67.14; 340/5.64, 825.72; 341/33; 702/150
See application file for complete search history.

(56) References Cited

U.S. PATENT DOCUMENTS

| 4,090,092 | A  | * | 5/1978  | Serrano ................... 200/600 |
| 6,047,163 | A  | * | 4/2000  | Miyoshi ................... 455/39 |
| 6,211,799 | B1 | * | 4/2001  | Post et al. ................ 341/33 |
| 6,223,018 | B1 | * | 4/2001  | Fukumoto et al. ........ 455/41.1 |
| 6,754,472 | B1 | * | 6/2004  | Williams et al. ......... 455/100 |
| 6,771,161 | B1 | * | 8/2004  | Doi et al. ................ 340/5.64 |
| 6,809,498 | B2 | * | 10/2004 | Nakamura et al. ........ 320/108 |
| 6,864,780 | B2 | * | 3/2005  | Doi et al. ................ 340/5.64 |

(Continued)

FOREIGN PATENT DOCUMENTS
JP   2001-125704 A   5/2001
(Continued)

OTHER PUBLICATIONS

Katsuyuki Fujii, et al; "Evaluation of the Received Signal Level in Relation to the Size and Carrier Frequencies of the Wearable Device Using Human Body as a Transmission Channel" Antennas and Propagation Society International Symposium, 2004, IEEE Jun. 20-25, 2004, vol. 1, pp. 105-108.

(Continued)

*Primary Examiner* — April G Gonzales
(74) *Attorney, Agent, or Firm* — Ladas & Parry LLP

(57) ABSTRACT

A communication device and method using the human body are provided. The communication device determines an arrangement direction of signal electrodes and ground electrodes according to a signal transmission direction and whether the ground electrodes come into contact with the human body according to a transmission/receiving distance and then performs data communication with the other communication device connected to the human body for the purpose of efficient human body communication.

7 Claims, 7 Drawing Sheets

U.S. PATENT DOCUMENTS

| | | | |
|---|---|---|---|
| 6,965,842 B2 * | 11/2005 | Rekimoto | 702/150 |
| 7,412,229 B2 * | 8/2008 | Ochiai et al. | 455/410 |
| 7,684,769 B2 * | 3/2010 | Song et al. | 455/100 |
| 2006/0092908 A1 * | 5/2006 | Sung et al. | 370/347 |
| 2010/0136906 A1 * | 6/2010 | Hwang et al. | 455/41.1 |
| 2010/0184373 A1 * | 7/2010 | Hebiguchi et al. | 455/41.1 |

FOREIGN PATENT DOCUMENTS

| | | |
|---|---|---|
| JP | 2002-009710 A | 1/2002 |
| JP | 2004-128746 A | 4/2004 |
| JP | 2004-186833 A | 7/2004 |

OTHER PUBLICATIONS

International Search Report—mailed Aug. 30, 2007; PCT/KR2007/002600.

* cited by examiner

COMMUNICATION DEVICE AND METHOD USING HUMAN BODY

TECHNICAL FIELD

The present invention relates to a communication device, and more particularly, to a communication device using the human body as a communication channel.

BACKGROUND ART

Many people carry PDAs, cellular phones, portable medical devices and so on with them all the time. To transmit data between these devices, a wired transmission method using cables and a wireless transmission method using radio waves and light are used.

The wired transmission method secures transmission data and has a high transmission rate but it has a shortcoming in that a user must carry a wired device such as a cable with him/her at all times. The wireless transmission method can easily transmit data but it requires additional circuits for wireless transmission and therefore it is difficult to reduce the cost of a communication device.

To solve the aforementioned problems, human body communication using the human body as a transmission medium has been recently proposed. That is, a signal output through a transmitter of a communication device is applied to the human body through an electrode connected to the human body and transmitted through the human body. The signal is received by a receiver of another communication device through another electrode connected to the human body. This human body communication is convenient to use because it does not need a wired device such as a cable and has an advantage in that it requires no additional circuits for wireless transmission.

Electrodes used for constructing a communication device for human body communication are divided into a signal electrode and a ground electrode based on their functions. The signal electrode is connected to an output signal line of a transmitter of the communication device or an input signal line of a receiver of the communication device in order to transmit a signal to the human body or to receive a signal from the human body. The ground electrode is connected to a grounding part of the communication device and affects the characteristics of signal transmission through the human body according to an arrangement direction of the signal electrode and the ground electrode and whether the ground electrode comes into contact with the human body.

DISCLOSURE OF INVENTION

Technical Problem

The present invention provides a communication method and device for minimizing a signal loss according to an arrangement direction of signal electrodes and ground electrodes and a transmission/receiving distance in order to achieve efficient human body communication.

Technical Solution

According to an aspect of the present invention, there is provided a communication device using the human body comprising an electrode unit including at least one electrode pair composed of a signal electrode and a ground electrode, the electrode pair being arranged in at least one direction; an electrode selecting switch selecting one of the at least one electrode pair; a transmitter outputting a data signal to the human body through the selected electrode pair; and a switch controller controlling the electrode selecting switch to transmit a test signal to the other communication device connected to the human body through the electrode pair to select an electrode pair having the smallest signal loss.

According to another aspect of the present invention, there is provided a communication method using the human body comprising transmitting a test signal to the other communication device connected to the human body through electrode pairs each composed of a signal electrode and a ground electrode, the electrode pairs being arranged in at least one direction; receiving information about an electrode pair having the smallest signal loss of the test signal from the other communication device; selecting an electrode pair based on the information received from the other communication device; and outputting a data signal to the human body through the selected electrode pair.

Advantageous Effects

According to the present invention, the arrangement direction of signal electrodes and ground electrodes is appropriately controlled according to a signal transmission direction. Also, whether the ground electrodes come into contact with the human body is controlled according to a transmission/receiving distance for the purpose of efficient human body communication.

BEST MODE

Figure 1:
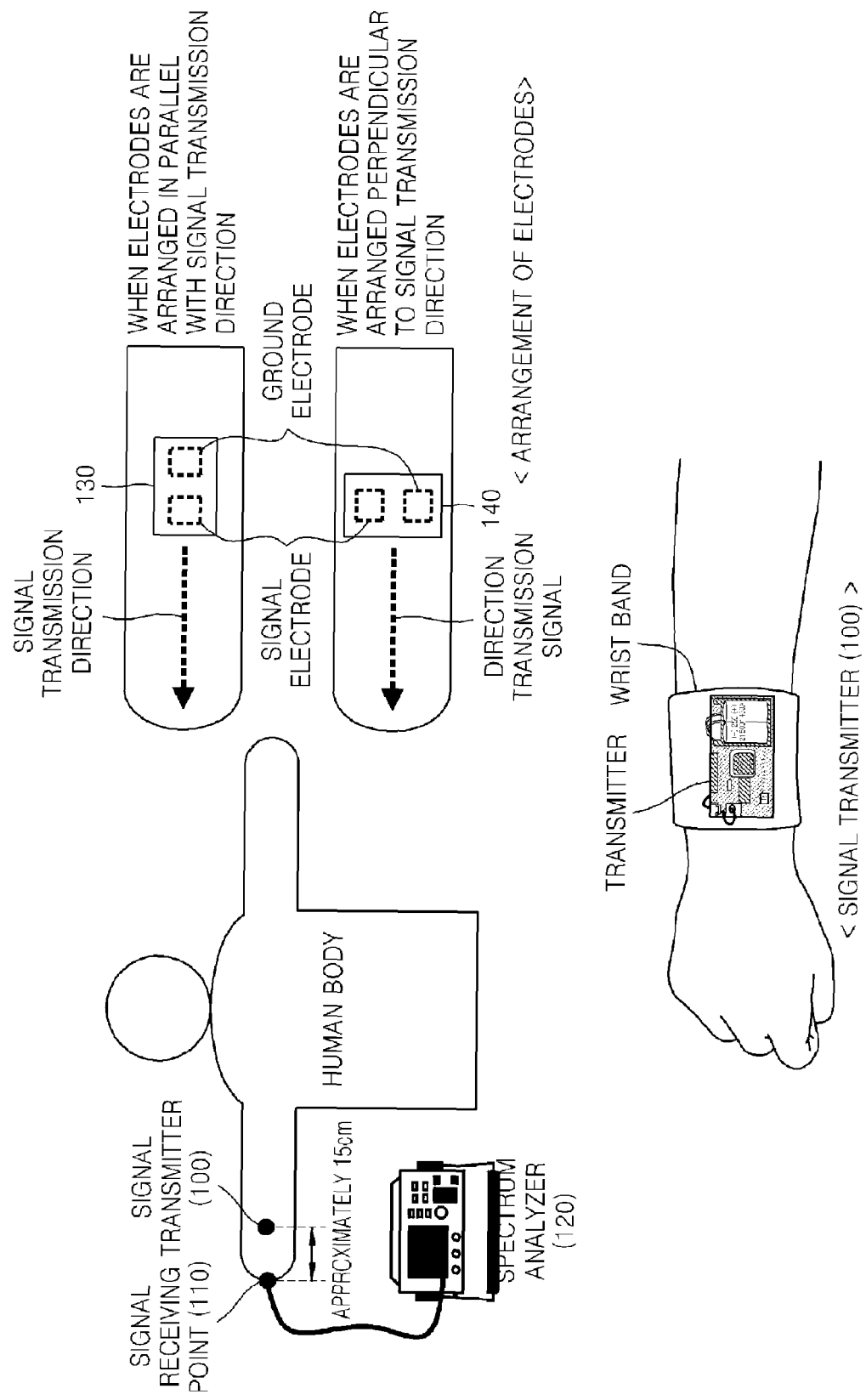
FIG. 1 illustrates a measurement environment for measuring a variation in signal loss according to an arrangement direction of signal electrodes and ground electrodes.

According to an aspect of the present invention, there is provided a communication device using the human body comprising an electrode unit including at least one electrode pair composed of a signal electrode and a ground electrode, the electrode pair being arranged in at least one direction; an electrode selecting switch selecting one of the at least one electrode pair; a transmitter outputting a data signal to the human body through the selected electrode pair; and a switch controller controlling the electrode selecting switch to transmit a test signal to the other communication device connected to the human body through the electrode pair to select an electrode pair having the smallest signal loss.

According to another aspect of the present invention, there is provided a communication method using the human body comprising transmitting a test signal to the other communication device connected to the human body through electrode pairs each composed of a signal electrode and a ground electrode, the electrode pairs being arranged in at least one direction; receiving information about an electrode pair having the smallest signal loss of the test signal from the other communication device; selecting an electrode pair based on the information received from the other communication device; and outputting a data signal to the human body through the selected electrode pair.

MODE OF INVENTION

The present invention will now be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art. Throughout the drawings, like reference numerals refer to like elements.

Figure 2:
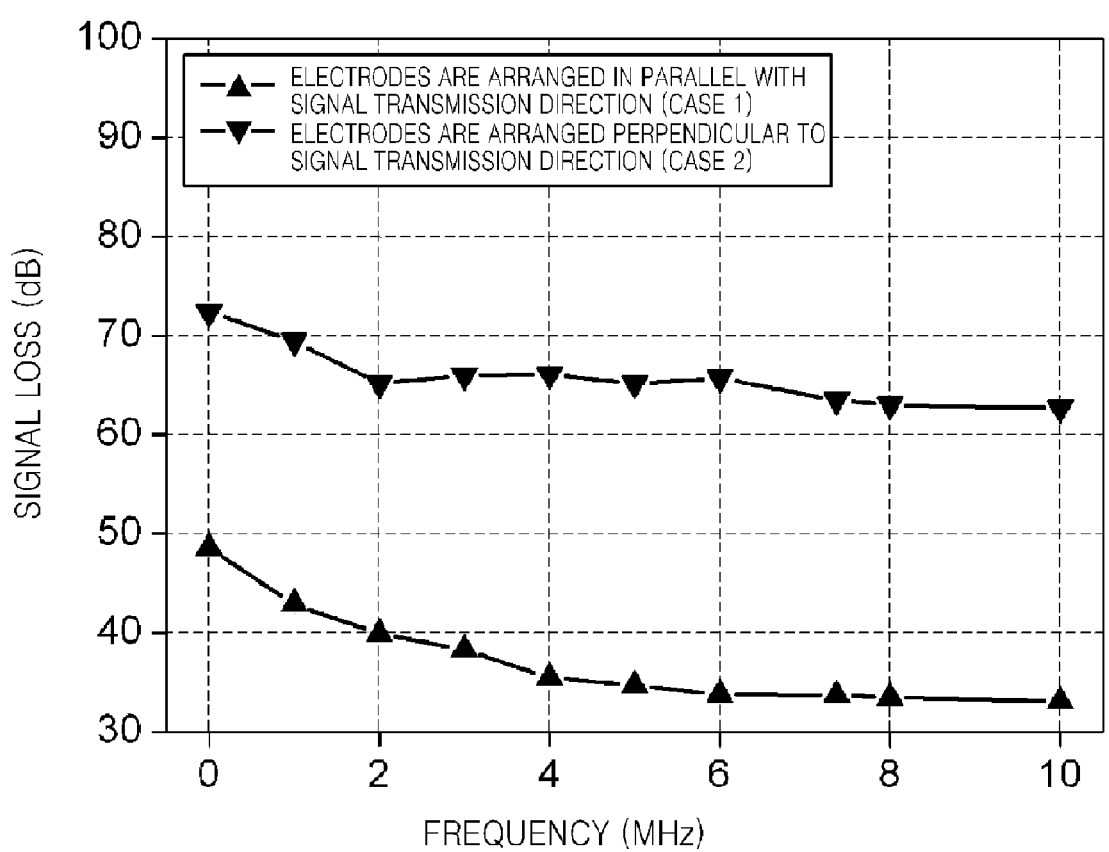
FIG. 2 is a graph illustrating the variation in signal loss, measured in the measurement environment illustrated in FIG. 1.

FIG. 1 illustrates a measurement environment for measuring a variation in signal loss according to an arrangement direction of signal electrodes and ground electrodes, and FIG. 2 is a graph illustrating the variation in signal loss, measured in the measurement environment illustrated in FIG. 1. Referring to FIG. 1, a signal transmitter 100 configured of a crystal oscillator is fixed to the right wrist of the human body using a wrist band, a transmission signal is applied to the human body, and the amount of loss of the signal transmitted through the human body is measured at the right fingertips (i.e., signal receiving point 110) using a spectrum analyzer 120. Particularly, a signal loss is measured for a case 130 where signal electrodes and ground electrodes are arranged in parallel with a signal transmission direction and a case 140 where the signal electrodes and the ground electrodes are arranged perpendicular to the signal transmission direction.

Referring to FIG. 2, it can be determined that the signal loss is smaller when the signal electrodes and the ground electrodes are arranged in parallel with the signal transmission direction than the signal loss when the signal electrodes and the ground electrodes are arranged perpendicular to the signal transmission direction. That is, a signal loss can be minimized and the communication device can be efficiently operated by arranging the signal electrodes and the ground electrodes in the signal transmission direction.

Figure 3:
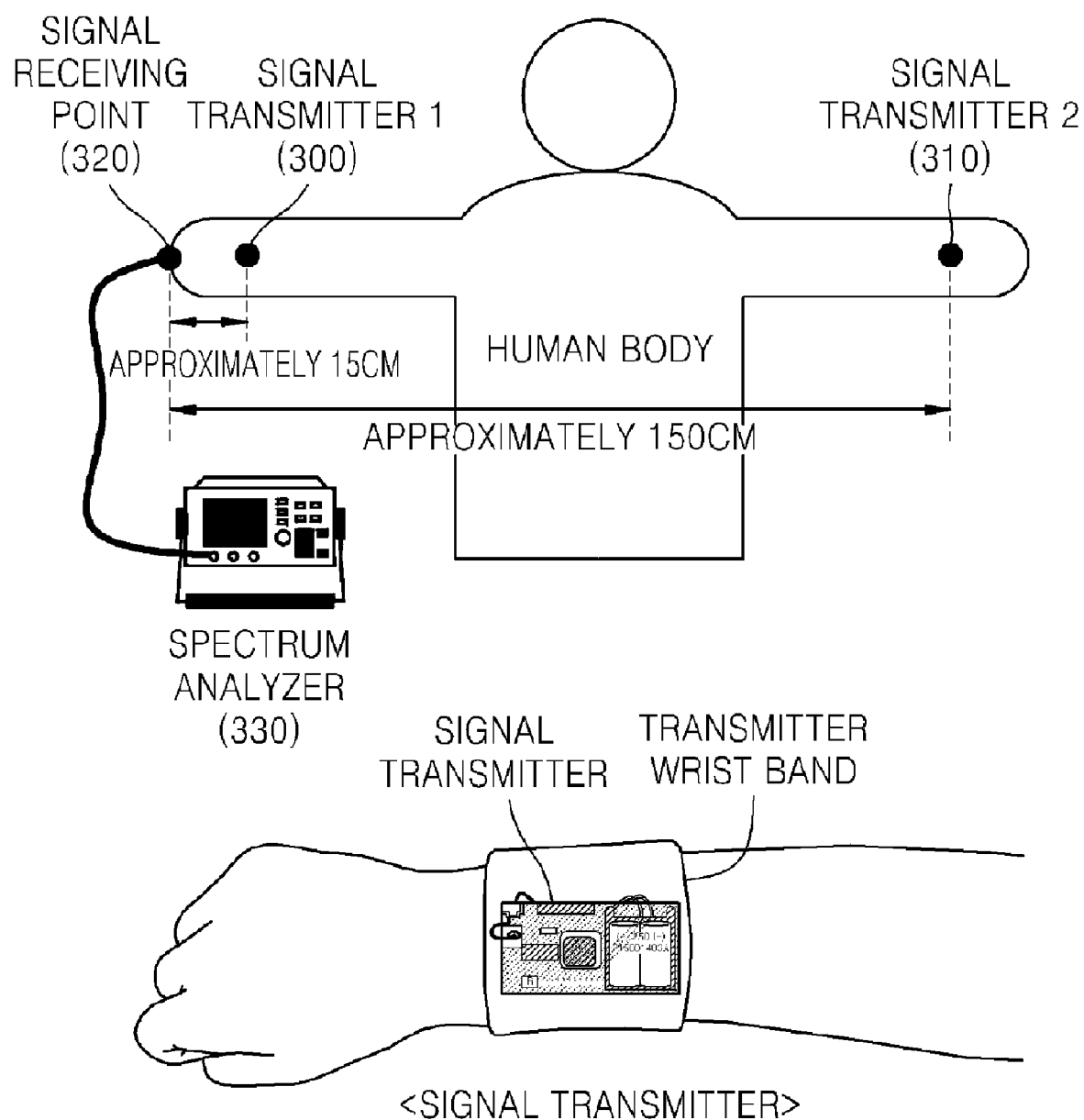
FIG. 3 illustrates a measurement environment for measuring a variation in signal loss according to whether ground electrodes come into contact with the human body or not.
Figure 4:
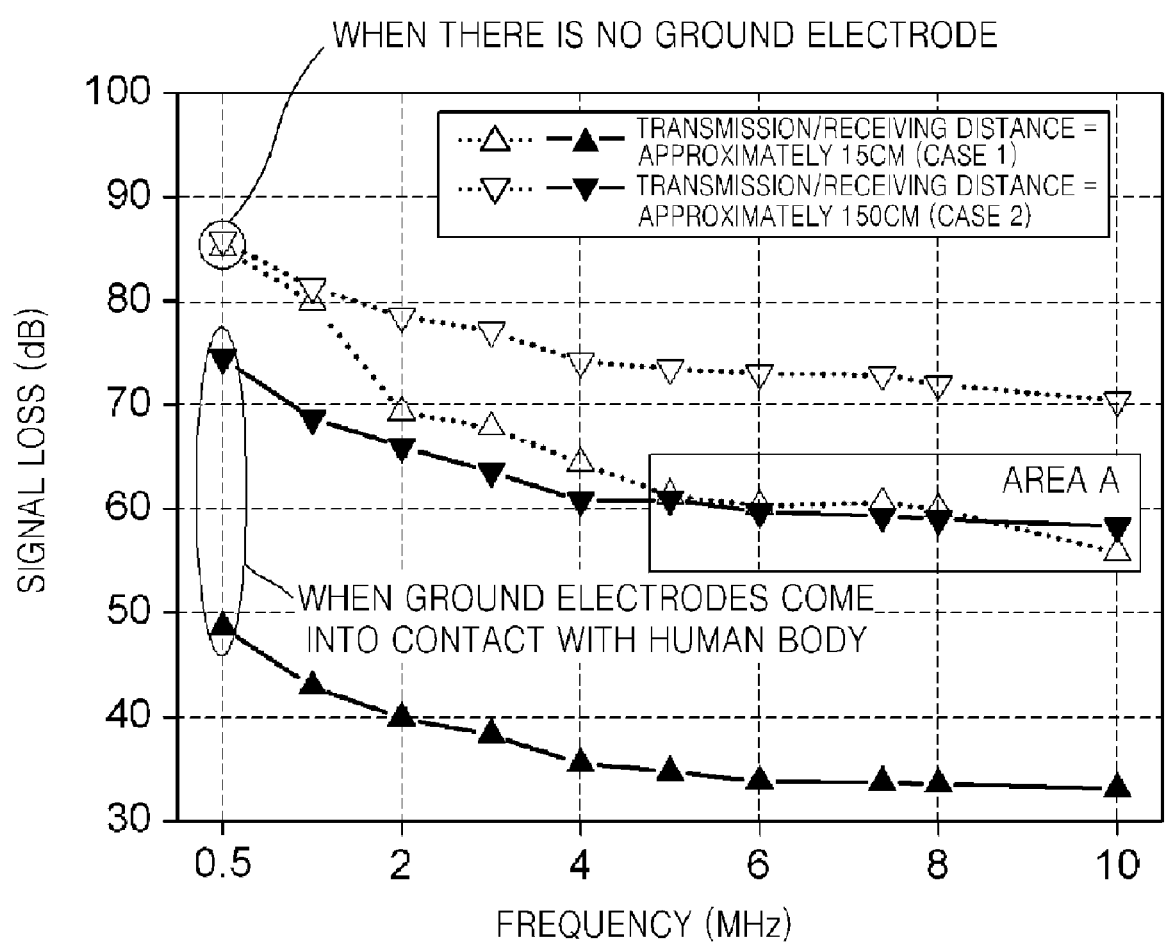
FIG. 4 is a graph illustrating the variation in signal loss, measured in the measurement environment illustrated in FIG. 3.

FIG. 3 illustrates a measurement environment for measuring a variation in signal loss according to whether the ground electrodes come into contact with the human body, and FIG. 4 is a graph illustrating the variation in signal loss, measured in the measurement environment illustrated in FIG. 3. Referring to FIG. 3, signal transmitters 300 and 310 which are each configured of a crystal oscillator are respectively fixed to the right wrist (transmission/receiving distance=15 cm approximately) and the left wrist (transmission/receiving distance=150 cm approximately) of the human body using wrist bands, and then a signal is applied to the human body. Then, the amount of loss of the signal transmitted through the human body is measured at the right fingertips 320 using a spectrum analyzer 330. Here, a signal loss is measured for a case where ground electrodes come into contact with the human body and a case where the ground electrodes do not come into contact with the human body.

Referring to FIG. 4, it is determined that the signal loss is decreased when the ground electrodes come into contact with the human body. However, the signal loss is reduced by approximately 25 dB as the ground electrodes come into contact with the human body when the transmitter is attached to the right wrist but the signal loss is decreased by only approximately 10 dB when the transmitter is attached to the left wrist. That is, a decrease in the signal loss, which occurs when the ground electrodes come into contact with the human body, is reduced as the transmission/receiving distance is increased.

In a region A illustrated in FIG. 4, case 1 and case 2 have almost the same signal loss. Accordingly, if a receiver for the human body communication is constructed so that the receiver can overcome a signal loss and restore a transmission signal when the transmission/receiving distance is long and the ground electrodes come into contact with the human body, signal restoration can be achieved even when the ground electrodes do not come into contact with the human body and the transmission/receiving distance is short. When the ground electrodes of the transmitter do not contact the human body, the current flowing between the signal electrodes and the ground electrodes is remarkably decreased. For example, approximately 16 mA flows between the signal electrodes and the ground electrodes at 3V when the ground electrodes come into contact with the human body in a band of 5 MHz while approximately 0.2 mA flows between the signal electrodes and the ground electrodes when the ground electrodes do not come into contact with the human body under the same conditions. Accordingly, power consumed in the transmitter can be reduced and the communication device can be efficiently operated by preventing the ground electrodes from coming into contact with the human body when the transmission/receiving distance is short, as described above.

Figure 5:
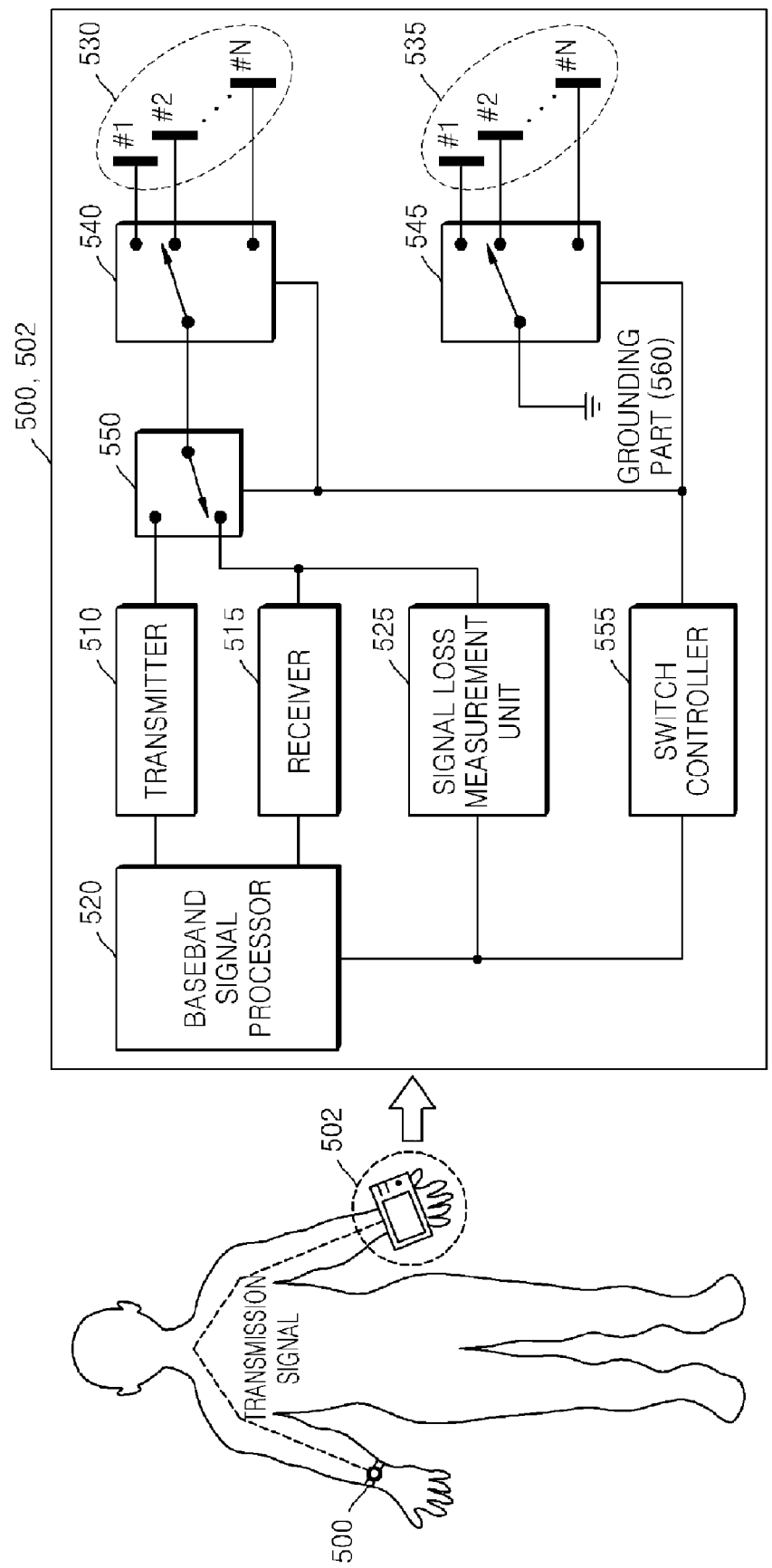
FIG. 5 illustrates a configuration of a communication device for human body communication according to an embodiment of the present invention.

FIG. 5 illustrates a configuration of a communication device for human body communication according to an embodiment of the present invention. Referring to FIG. 5, first and second communication devices 500 and 502 are attached to the human body in order to transmit and receive data through the human body. The first and second communication devices 500 and 502 includes a transmitter 510 and a receiver 515 for transmitting and receiving a signal, a baseband signal processor 520 for processing a baseband signal, a signal loss measurement unit 525 for measuring a signal loss, a plurality of pairs of signal electrodes 530 and ground electrodes 535, a switch 550 for selecting a transmission/receiving signal, electrode selecting switches 540 and 545 for selecting a pair of a signal electrode and a ground electrode, and a switch controller 555 for controlling the switches.

The transmitter 510 and the receiver 515 can be implemented using a conventional transmitter and receiver used for human body communication and therefore detailed descriptions of the transmitter 510 and the receiver 515 are omitted.

The first and second communication device 500 and 502 for the human body communication system can be attached to an arbitrary point of the human body, and thus a transmission/receiving distance can vary according to the application of human body communication. Most communication devices are located in arbitrary directions so that signal electrodes and ground electrodes of the communication devices are not arranged in parallel with a signal transmission direction in many cases. For the most efficient signal transmission, the arrangement direction of the signal electrodes and the ground electrodes and whether the ground electrodes come into contact with the human body in response to a transmission/receiving distance must be appropriately controlled.

Operations of the first and second communication devices 500 and 502 attached to the human body for selecting an electrode arrangement to ensure efficient signal transmission before transmitting and receiving data through the human body will now be explained. Here, the communication devices 500 and 502 have the same configuration, and thus components of the communication devices are represented by the same reference numerals.

The switch controller 555 of the first communication device 500 controls the electrode selecting switches 540 and 545 to select a signal electrode 530 and ground electrode 535 pair. The switch 550 selects the transmitter 510 of the first communication device 500 and the transmitter 510 transmits a test signal having an arbitrary waveform in order to measure signal loss through the human body.

In the second communication device 502 receiving the test signal from the first communication device 500, the switch 550 selects the signal loss measurement unit 525 and it measures a loss of the received test signal, and the baseband signal processor 520 of the second communication device 502 stores the measured signal loss.

By this operation, a signal loss is measured for all the electrode pairs and stored. The second communication device 502 compares the stored signal loss measurement values and transmits the numeral corresponding to the electrode pair having the smallest signal loss to the first communication device 500. The electrode pair having the smallest signal loss are electrodes arranged in parallel with the signal transmission direction. Using this electrode pair enables efficient signal transmission by minimizing signal loss.

After selecting the electrode pair, it is determined whether the ground electrodes come into contact with the human body. Specifically, the switch controller 555 of the first communication device 500 controls the electrode selecting switch 545 to disconnect the ground electrodes 535 from a grounding part 560 of the first communication device 500, achieving an effect whereby the ground electrodes 535 do not come into contact with the human body. The transmitter 510 of the first communication device 500 transmits a test signal having an arbitrary waveform in order to measure signal loss through the human body while the ground electrodes 535 are not in contact with the human body.

The signal loss measurement unit 525 of the second communication device 502 measures a loss of the test signal received through the human body. The receiver 515 of the second communication device 502 compares the signal loss measured by the signal loss measurement unit 525 of the second communication device 502 to a maximum signal loss required for restoring a transmission signal. The maximum signal loss is proportional to the sensitivity of the communication device and determined by the performance of the receiver 515 of the communication device.

When the measured signal loss is greater than the maximum signal loss, the second communication device 502 transmits a specific signal indicating that the measured signal loss is greater than the maximum signal loss to the first communication device 500. The switch controller 555 of the first communication device 500 controls the electrode selecting switch 545 to connect the ground electrodes 535 to the grounding part 560 when receiving the specific signal.

When the measured signal loss is smaller than the maximum signal loss, the second communication device 502 transmits a specific signal indicating that the measured signal loss is smaller than the maximum signal loss to the first communication device 500. Then, the switch controller 555 of the first communication device 500 controls the electrode selecting switch 545 to maintain the disconnection of the ground electrodes 535 from the grounding part 560 when receiving the specific signal indicating that the measured signal loss is smaller than the maximum signal loss.

Only a very small current flows between the signal electrodes 530 and the ground electrodes 535 when the ground electrodes 535 do not come into contact with the human body, so the power consumption of the communication devices can be reduced, resulting in efficient signal transmission.

Figure 6:
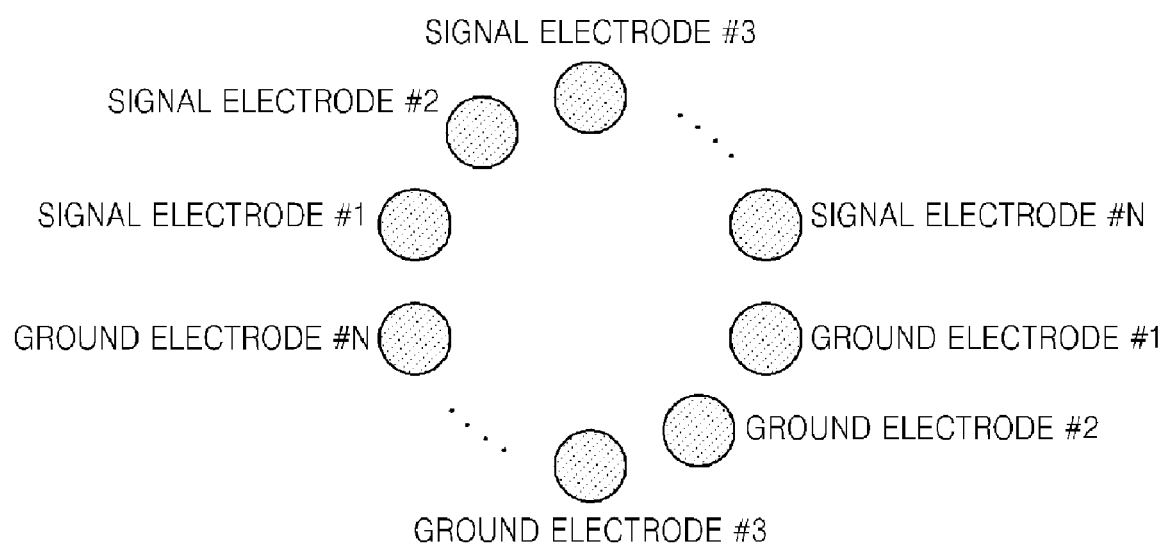
FIG. 6 illustrates an example of an arrangement of signal electrodes and ground electrodes according to an embodiment of the present invention.

FIG. 6 illustrates an example of an arrangement of signal electrodes and ground electrodes according to an embodiment of the present invention. Referring to FIG. 6, a signal transmission direction varies with the direction in which a communication device is placed. Thus, a plurality of signal electrodes and ground electrodes in pairs are radially arranged. However, the arrangement direction of the electrodes can be appropriately varied according to the field of application to which the human body communication is applied. Furthermore, the size and number of electrodes are appropriately controlled according to the area to which the electrodes are attached in the communication device.

Figure 7:
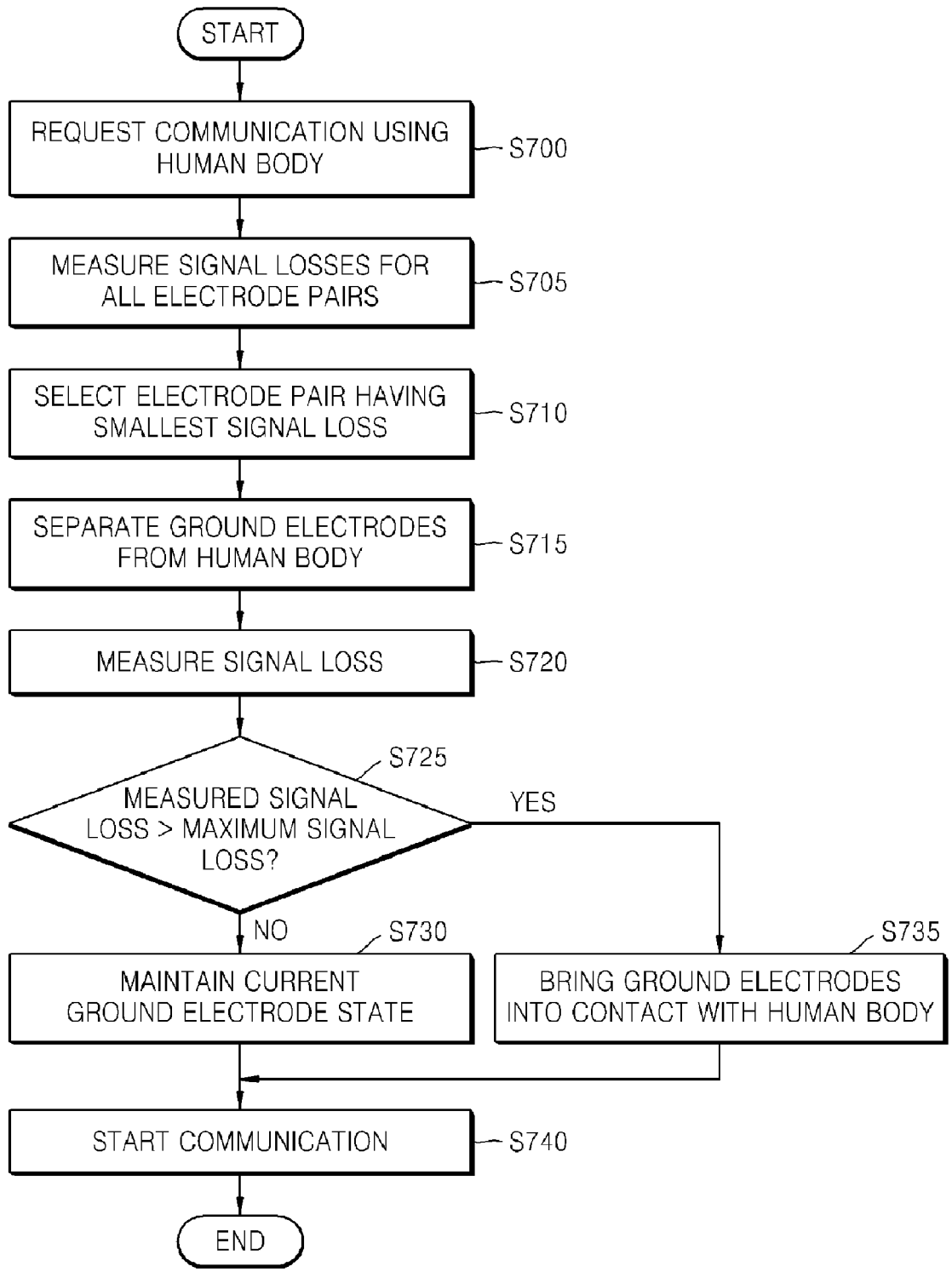
FIG. 7 is a flow chart of a communication method using the human body according to an embodiment of the present invention.

FIG. 7 is a flow chart of a communication method using the human body according to an embodiment of the present invention. Referring to FIG. 7, when data communication between first and second communication devices attached to the human body is requested in step S700, the first communication device intended to transmit data transmits a test signal to the second communication device through electrode pairs each composed of a signal electrode and a ground electrode, arranged in various directions, in order to measure signal losses for all the electrode pairs in step S705. Then, the first communication device selects an electrode pair having the smallest signal loss in step S710.

Subsequently, the first communication device separates the ground electrodes from the human body (separates the ground electrodes from the grounding part in the case of FIG. 5) in step S715 and then transmits the test signal to the second communication device in order to measure a signal loss in step S720. When the measured signal loss is greater than a maximum signal loss required for signal restoration in step S725, the ground electrodes come into contact with the human body in step S725. When the measured signal loss is smaller than the maximum signal loss in step S725, the current state in which the ground electrodes are separated from the human body is maintained in step S730.

When the arrangement direction of the signal electrodes and the ground electrodes is determined, as well as whether the ground electrodes come into contact with the human body, through the aforementioned process, data communication between the first and second communication devices is carried out in step S740.

According to the present invention, the arrangement direction of signal electrodes and ground electrodes is appropriately controlled according to a signal transmission direction. Also, whether the ground electrodes come into contact with the human body is controlled according to a transmission/receiving distance for the purpose of efficient human body communication.

While the present invention has been particularly shown and described with reference to exemplary embodiments thereof, it will be understood by those of ordinary skill in the art that various changes in form and details may be made therein without departing from the spirit and scope of the present invention as defined by the following claims.

INDUSTRIAL APPLICABILITY

The present invention provides a communication method and device for minimizing a signal loss according to an arrangement direction of signal electrodes and ground electrodes and a transmission/receiving distance in order to achieve efficient human body communication.

The invention claimed is:

1. A communication device using a human body comprising:
    an electrode unit including a plurality of electrode pairs, wherein each of the plurality of electrode pairs is composed of a signal electrode and a ground electrode,
    wherein each of the plurality of electrode pairs are arranged radially,
    wherein each of the plurality of electrode pairs are in the communication device,
    and
    wherein each of the plurality of radially arranged electrode pairs are each arranged in order to a have a data signal transmitted a direction mutually exclusive of any of the other electrode pairs;
    an electrode selecting switch selecting one of the plurality of electrode pairs;
    a transmitter outputting the data signal to the human body through the selected electrode pair; and
    a switch controller controlling the electrode selecting switch to select an electrode pair from the plurality of electrode pairs having a smallest measured signal loss from each of a plurality of signal losses measured from each of the plurality of electrode pairs to an other communication device, which is measured by transmitting a test signal to the other communication device connected to the human body through each of the plurality of electrode pairs.

2. The communication device of claim 1, wherein the electrode selecting switch selects whether the ground electrode is connected to a grounding part of the communication device, and the switch controller controls the electrode selecting switch to connect the ground electrode to the grounding part when a signal loss, measured by transmitting a second test signal to the other communication device while the ground electrode is disconnected from the grounding part, is greater than a maximum signal loss required for signal restoration.

3. The communication device of claim 1, further comprising:
    a signal loss measurement unit measuring the signal loss of the test signal transmitted through each of the plurality of electrode pairs; and
    a baseband signal processor detecting the electrode pair having the smallest signal loss from among the measured signal losses and transmitting information about the detected electrode pair to the other communication device.

4. A communication method using a human body comprising:
    transmitting a test signal to a other communication device connected to the human body,
    wherein the test signal is transmitted through a plurality of electrode pairs,
    wherein each of the electrode pairs are composed of a signal electrode and a ground electrode,
    wherein each of the plurality of electrode pairs are arranged radially,
    and
    wherein each of the plurality of radially arranged electrode pairs are each arranged in order to a have a data signal transmitted in a direction mutually exclusive of any of the other electrode pairs;
    receiving information about an electrode pair from the plurality of electrode pairs having a smallest measured signal loss from each of a plurality of signal losses measured from each of the plurality of electrode pairs to an other communication device, which is measured from a test signal being transmitted from each of the plurality of electrode pairs in the communication device to the other communication device, and
    wherein the measurement from the test signal is configured while each of the plurality of electrode pairs in the communication device are connected to the human body;
    selecting an electrode pair having the smallest measured signal loss, which is based on the information received from the other communication device;
    outputting a data signal to the human body through the selected electrode pair, and
    wherein after selecting the electrode pair, determining whether the ground electrode of the selected electrode pair remains connected to the grounding part by comparing a signal loss of a second test signal sent from the communication device to the other communication device to a maximum signal loss required for signal restoration from the other communication device.

5. The communication method of claim 4, further comprising:
    disconnecting the ground electrodes from a grounding part of the communication device of the selected electrode pair;
    transmitting the second test signal from the communication device to the other communication device;
    receiving the result obtained by comparing a signal loss of the second test signal to the maximum signal loss required for signal restoration from the other communication device; and
    determining whether the ground electrode of the selected electrode pair is connected to the grounding part based on the received result.

6. The communication method of claim 5, wherein the determining whether the ground electrode of the selected electrode pair is connected to the grounding part comprises:
    connecting the ground electrode to the grounding part when the signal loss of the test signal is greater than the maximum signal loss; and
    maintaining disconnection of the ground electrode from the grounding part when the signal loss of the test signal is smaller than the maximum signal loss.

7. A communication device using the human body comprising:
    an electrode unit including a plurality of electrode pairs, wherein each of the plurality of electrode pairs is composed of a signal electrode and a ground electrode,
    wherein each of the plurality of electrode pairs are arranged radially,
    wherein each of the plurality of electrode pairs are 180 degrees apart from each other,
    wherein each of the plurality of radially arranged electrode pairs being 180 degrees apart from each other are each arranged in a direction mutually exclusive of each other;
    an electrode selecting switch selecting one of the plurality of electrode pairs;
    a transmitter outputting a data signal to the human body through the selected electrode pair; and
    a switch controller controlling the electrode selecting switch to select an electrode pair from the plurality of electrode pairs having a smallest measured signal loss from each of a plurality of signal losses measured from each of the plurality of electrode pairs to an other communication device, which is measured by transmitting a test signal to the other communication device connected to human body through each of the plurality of electrode pairs, and wherein the test signal is only transmitted within the human body from the communication device to the other communication device while each of the plurality of electrode pairs in the communication device are connected to the human body.

* * * * *